(12) United States Patent
Lu

(10) Patent No.: US 7,611,489 B2
(45) Date of Patent: Nov. 3, 2009

(54) SAFETY SYRINGE

(76) Inventor: Feng-Hui Lu, No. 5, Alley 4, Lane 46, -Xianzheng Rd., Lingya Dist., Kaohsiung City (TW)

(*) Notice: Subject to any disclaimer, the term of this patent is extended or adjusted under 35 U.S.C. 154(b) by 148 days.

(21) Appl. No.: 12/004,978

(22) Filed: Dec. 26, 2007

(65) Prior Publication Data

US 2009/0171286 A1 Jul. 2, 2009

(51) Int. Cl.
*A61M 5/00* (2006.01)
*A61M 5/24* (2006.01)

(52) U.S. Cl. .................. 604/110; 604/200; 604/203

(58) Field of Classification Search .......... 604/110, 604/191, 201, 203, 221, 222, 228, 229, 231, 604/243, 244, 241, 91
See application file for complete search history.

(56) References Cited

U.S. PATENT DOCUMENTS 4,331,146 A * 5/1982 Brignola ............... 604/200

* cited by examiner

*Primary Examiner*—Nicholas D Lucchesi
*Assistant Examiner*—Leah Stohr
(74) *Attorney, Agent, or Firm*—Frenkel & Associates, P.C.

(57) ABSTRACT

A safety syringe includes a barrel which has a hollow passage inside and is coupled with a barrel cover. A push rod has a distal end coupled with a rubber ring to form a close contact with the hollow passage in a slidable manner. A driving module has an inner detent member, a piston seat and a piston rubber ring held in the barrel cover. The push rod is movable forwards to push the inner detent member and the piston rubber ring of the driving module forwards to make a cut surface at one end of the push rod to hit one end of a first stem of the needle mount to be broken and separated so that continuous moving forward of the push rod causes instant release of air pressure inside to retract the needle mount in a holding chamber of the push rod to safely hold a needle after injection.

8 Claims, 11 Drawing Sheets

US 7,611,489 B2

SAFETY SYRINGE

FIELD OF THE INVENTION

The present invention relates to a safety syringe and particularly to a syringe that has a plunger with a breaking surface formed at a distal end to be pressed and broken by one end of a first stem of a needle seat in a separated condition so that air pressure in the syringe resulting from continuous thrust of the plunger can be released instantly to retract and hold the needle seat in a holding chamber of the plunger in a safer condition.

BACKGROUND OF THE INVENTION

Applicant has previously submitted a patent application about syringe (U.S. patent application Ser. No. 11/349,189) which includes a barrel A10, a push rod A20, a driving module A30 and a needle mount A40. The barrel A10 has a hollow passage A11 inside and is coupled with a barrel cover A12. The push rod A20 has one end wedged with a pad A24 on the periphery to form a close contact with the hollow passage A11 in a slidable fashion. The barrel cover A12 houses a plunger A31, the driving module A30 of a piston pump A32 and the needle mount A40 held in the piston pump A32 that has a cut surface A412. Patents have been granted for that application in Germany and Taiwan. It is widely appreciated in the medical field. The present invention aims to provide an improvement over the aforesaid patent with fewer elements, at a lower cost and to hold a needle A45 after injection.

SUMMARY OF THE INVENTION

The primary object of the present invention is to provide a safety syringe which has a push rod with a distal end to push an inner detent member and a piston rubber ring of a driving module forwards so that the distal end with a cut surface formed thereon is pressed against one end of a first stem of a needle mount to be broken and separated such that the push rod can be moved continuously forwards until reaching the top end of the first stem to allow the piston rubber ring to be separated from the needle mount so that internal gas pressure can be released quickly to retract the needle mount into a holding chamber of the push rod to safely hold a needle after injection.

The safety syringe according to the invention includes a barrel, a push rod, a driving module and a needle mount. The barrel has a hollow passage inside and is coupled with a barrel cover. The push rod has a distal end coupled with a rubber ring to form a close contact with the hollow passage of the barrel in a slidable manner. The driving module has an inner detent member, a piston seat and a piston rubber ring held in the barrel cover. The inner detent member and the piston rubber ring are run through by the needle mount in the center.

By means of the construction set forth above, many benefits can be achieved, notably:

1. Improved safety: The inner detent member and piston rubber ring can be moved forwards due to pushing of the push rod so that the cut surface at the distal end of the push rod hits one end of the first stem of the needle mount to be broken and separated. The push rod can be continuously moved forwards until reaching the top end of the needle mount to separate the piston rubber ring and the needle mount. Hence internal gas pressure can be released quickly to retract the needle mount into the holding chamber of the push rod to hold the needle after injection. Safety improves.

2. Improved injection effect: With the barrel encased by the barrel cover and the needle mounted onto the needle mount retracted and held in the holding chamber of the push rod, the barrel cover can be covered by an upper cap. Thus the incident of hurting people that might otherwise occur during recycling and transportation can be prevented, and safety is further enhanced.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENT

Figure 1:
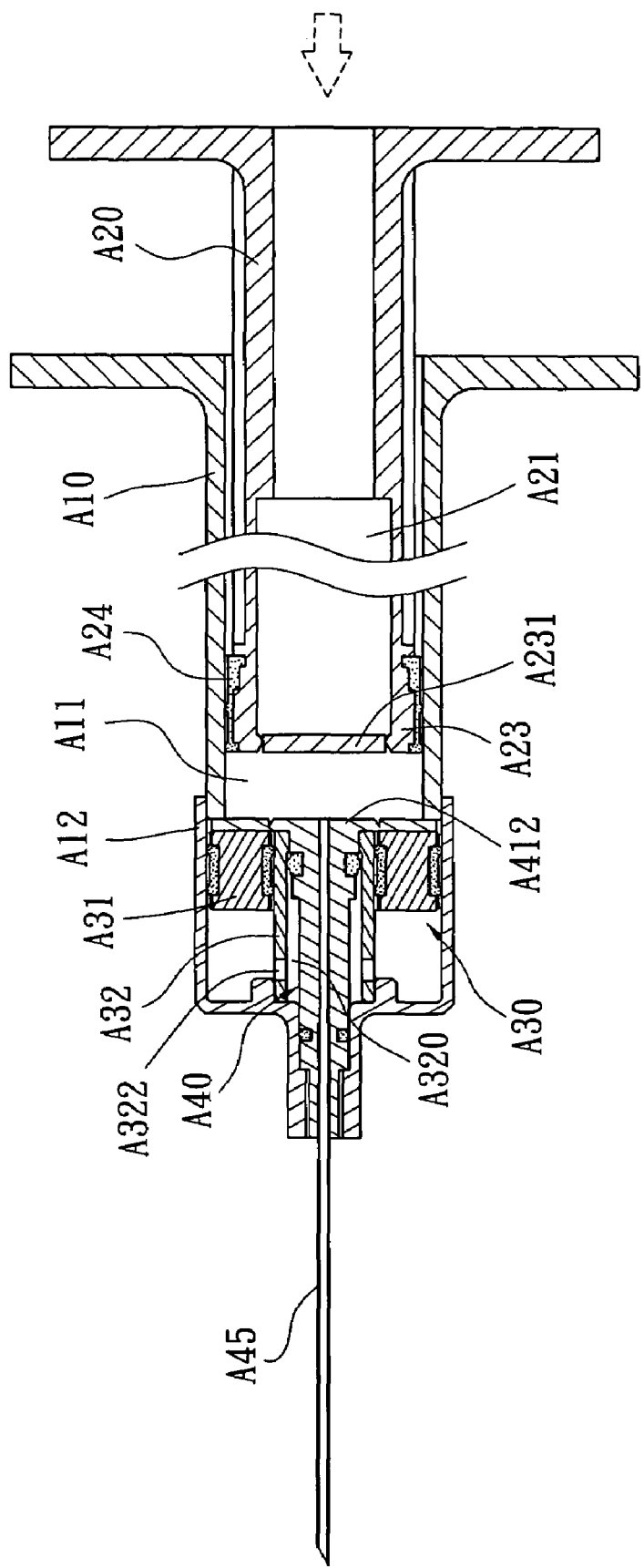
FIG. 1 is a schematic view of a conventional safety syringe with the push rod in a push forward condition-1.
Figure 2:
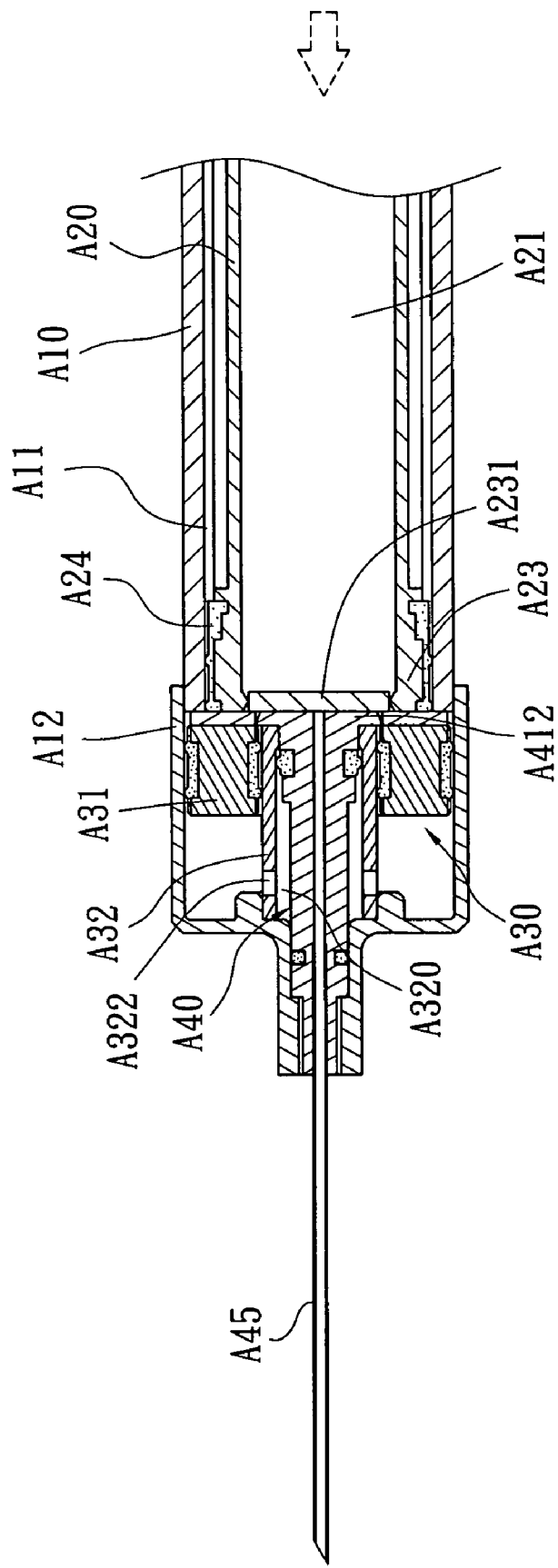
FIG. 2 is a schematic view of a conventional safety syringe with the push rod in a push forward condition-2.
Figure 3:
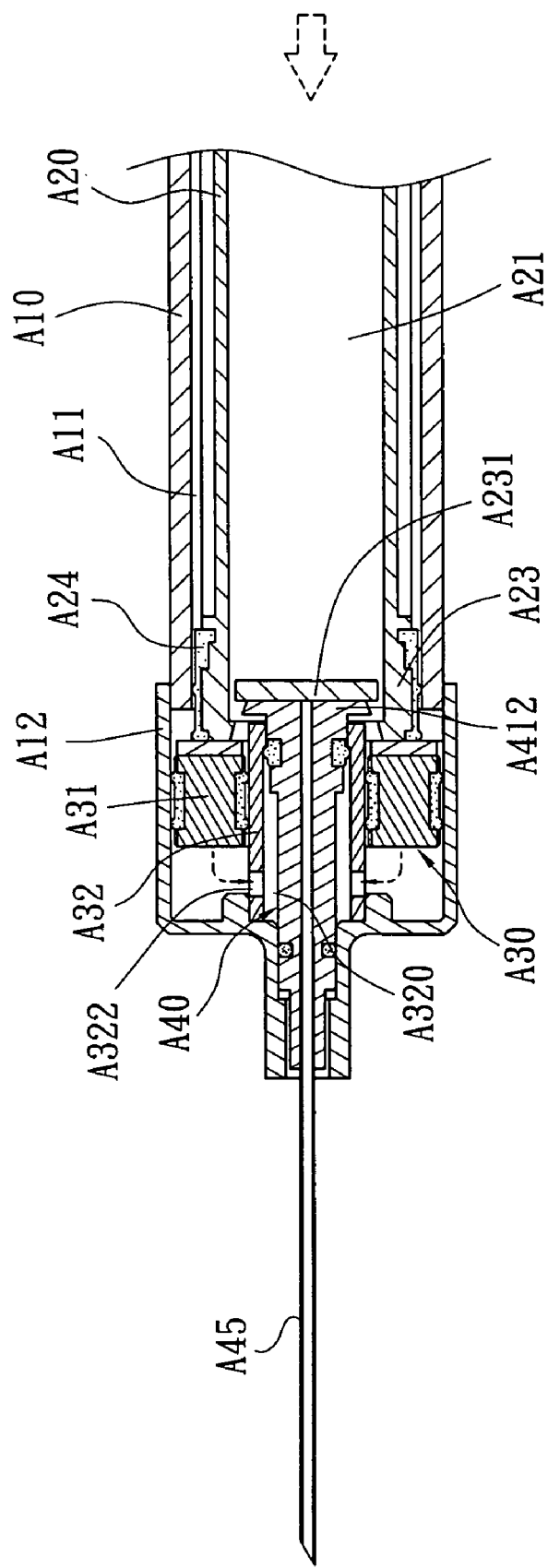
FIG. 3 is a schematic view of a conventional safety syringe with the push rod in a push forward condition-3.
Figure 4:
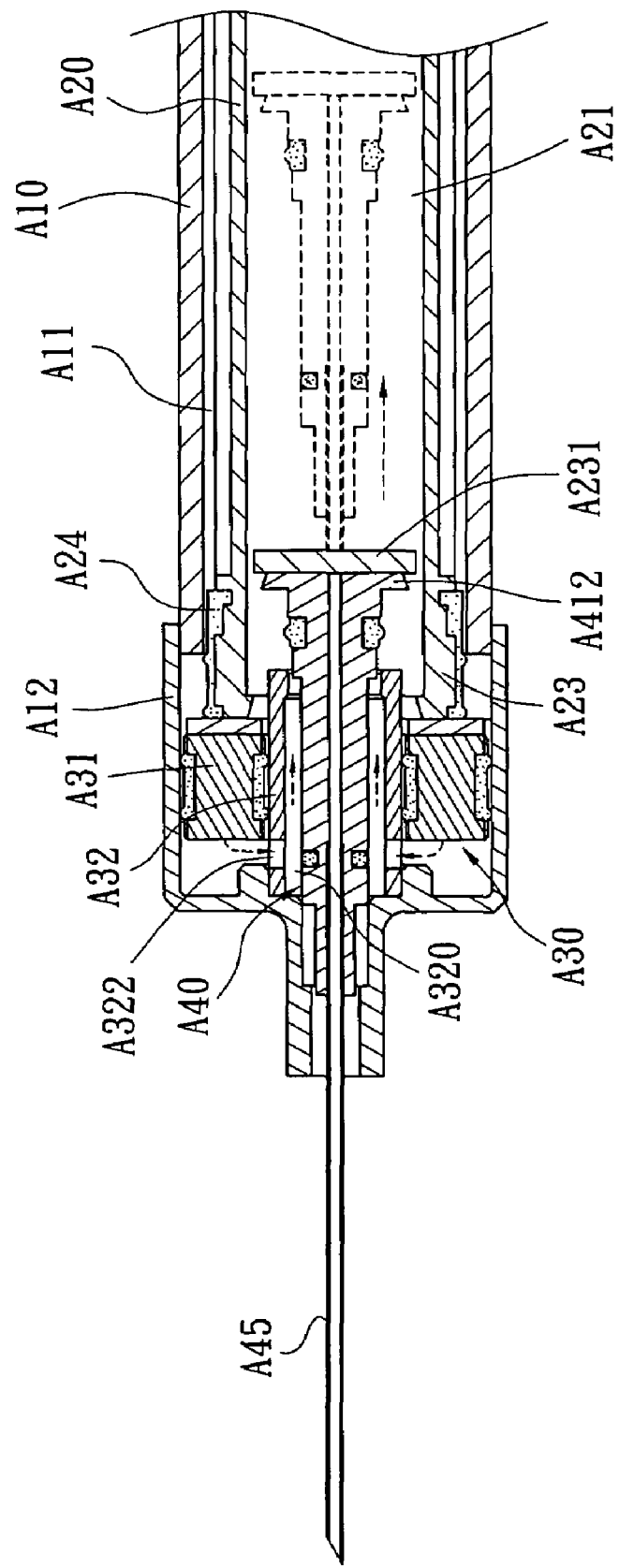
FIG. 4 is a schematic view of a conventional syringe with the needle mount held inside at a greater air pressure.
Figure 5:
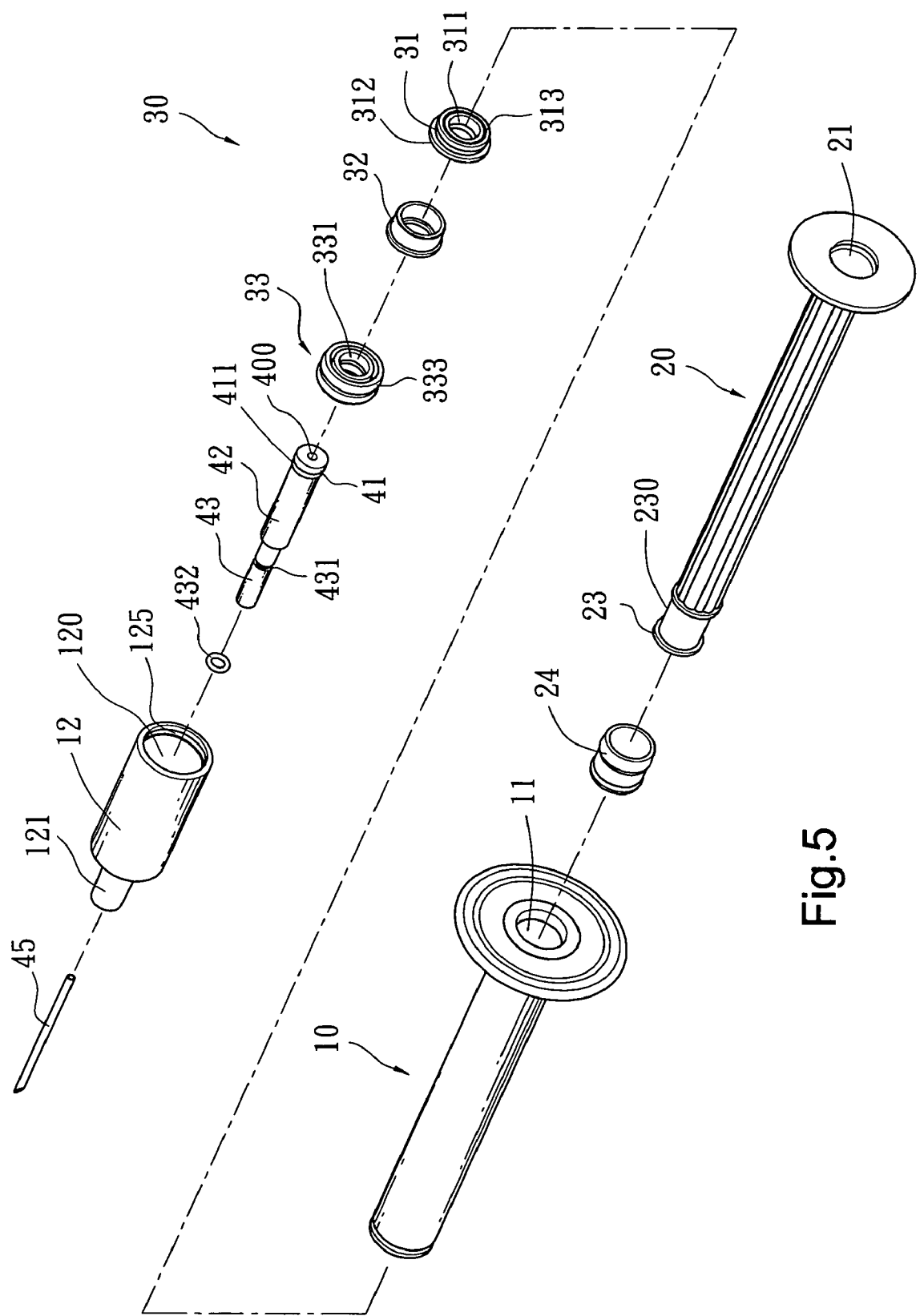
FIG. 5 is an exploded view of the safety syringe of the invention.
Figure 6:
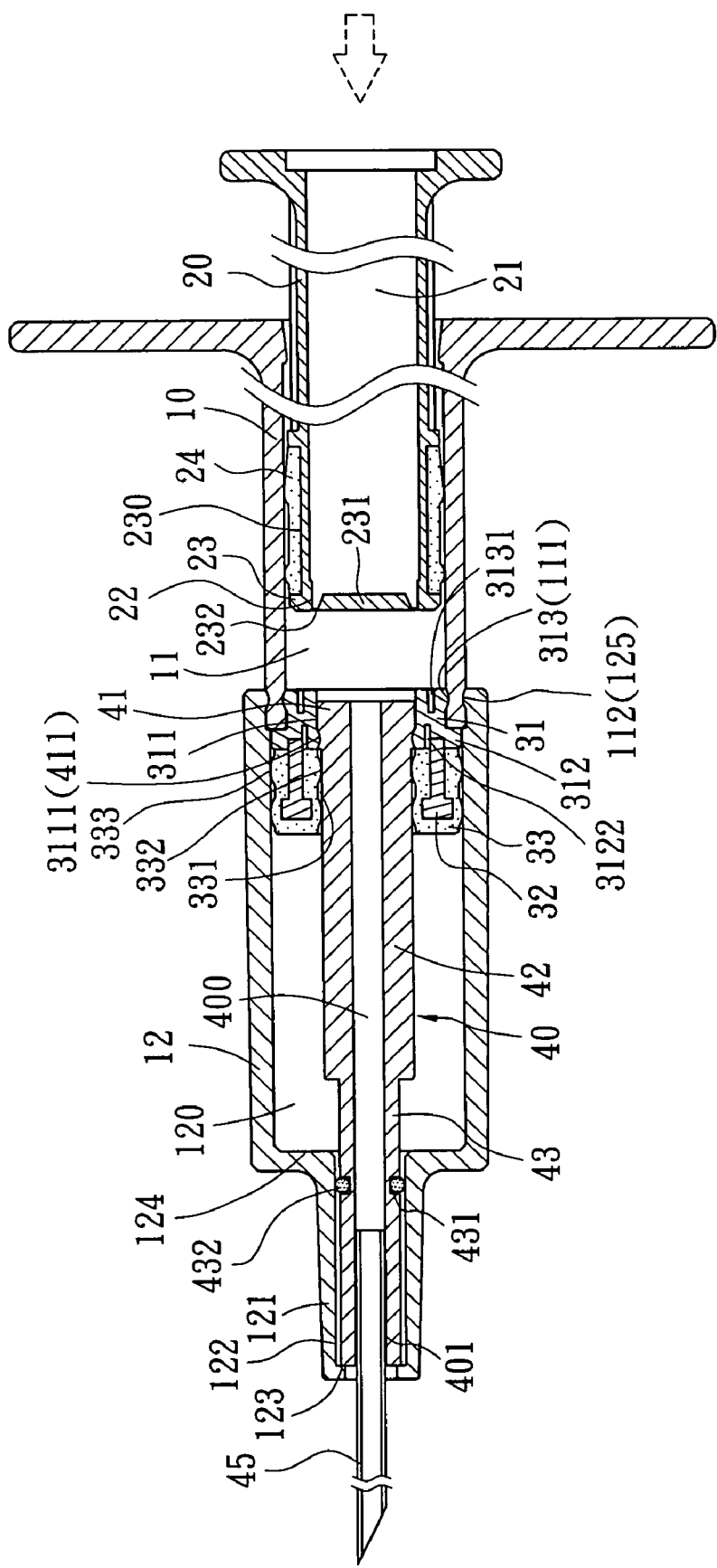
FIG. 6 is a schematic view of the invention with the push rod in a push forward condition-1.

Please refer to FIGS. 5 and 6, the present invention mainly includes a barrel 10, a push rod 20, a driving module 30 and a needle mount 40.

The barrel 10 has a hollow passage 11 inside, and one end with annular grooves 111 and 112 formed on an inner wall and an outer wall opposing each other. The barrel at the one end further is coupled with a barrel cover 12 which has a protruding end 121 at one end with a housing chamber 120 formed inside. The protruding end 121 has a through hole 122 which has a first pressing surface 123 and a second pressing surface 124 spaced from the first pressing surface 123 and formed at a greater diameter. The barrel cover 12 has another end with an annular flange 125 formed on an inner wall to be wedged with the annular groove 112 of the barrel 10.

The push rod 20 is held in the hollow passage 11 in a close contact and slidable manner. It has a holding chamber 21 with a bucking surface 22 formed thereon and a distal end 23 with an annular trough 230 formed on the periphery to be coupled with a rubber ring 24. The distal end 23 has two sides forming respectively a cut surface 231 and an indented rim 232.

The driving module 30 is held in the barrel cover 12, and includes an inner detent member 31, a piston seat 32 and a piston rubber ring 33. The inner detent member 31 has an aperture 311 and an annular bulged element 3111, an annular ring 312 at one end, and a wedge groove 3121 and an extensible first groove 3122 at one end close to the annular ring 312, and a flange 313 at another end to wedge in the annular groove 111 of the barrel 10, and also an extensible second groove 3131 at the another end surface. The piston seat 32 is protrusive and has one end wedged in the wedge groove 3121 of the inner detent member 31. The piston rubber ring 33 is adjacent to the inner detent member 31 and has a through hole 331 formed therein and one or more jutting rings 332 and 333 formed on the inner and outer periphery to hold the piston seat 32. Thus the piston rubber ring 33 is wedged in the piston seat 32 and does not deform easily.

The needle mount 40 is coupled with the inner detent member 31 and held in the piston rubber ring 33, and has a first stem 41, a second stem 42 and a third stem 43 of different diameters at one end, and a through hole 400 formed inside, and a holding port 401 at one end to hold a needle 45. The first stem 41 has an annular groove 411 on the periphery to be coupled with the aperture 311 and annular bulged element 3111 of the inner detent member 31. The second stem 42 has one end inserted in the through hole 331 of the piston rubber ring 33 in contact with the jutting ring 332 at the inner periphery. The third stem 43 has an annular groove 431 on the periphery to hold an O-ring 432 to be coupled with the through hole 122 of the protruding end 121 of the barrel cover 12, and has a top end pressing the first pressing surface 123.

Figure 7:
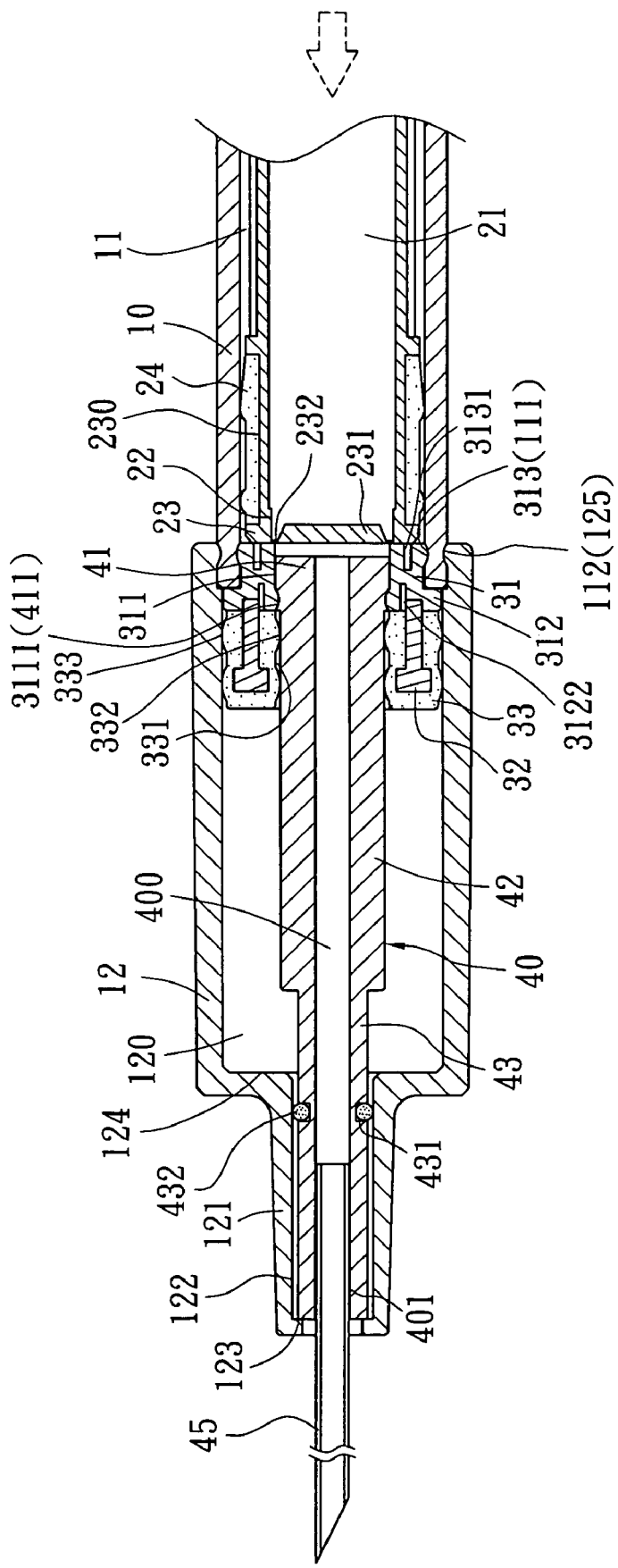
FIG. 7 is a schematic view of the invention with the push rod in a push forward condition-2.
Figure 8:
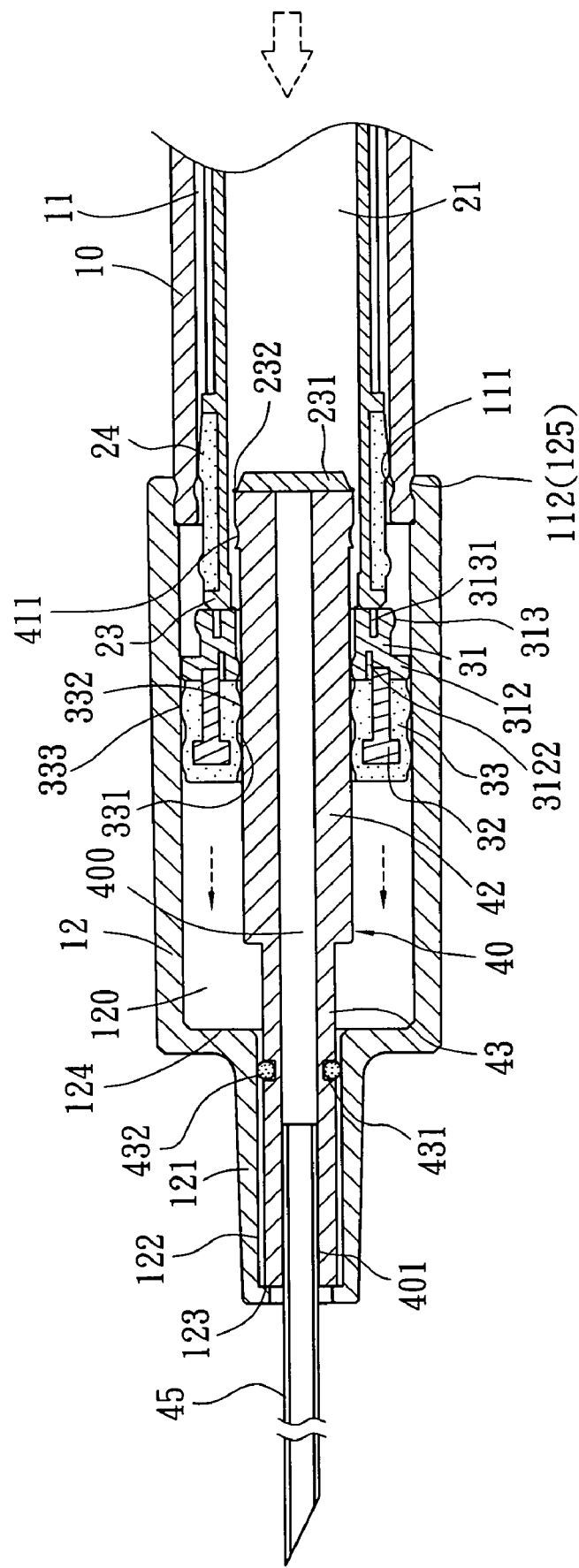
FIG. 8 is a schematic view of the invention with the push rod in a push forward condition-3.
Figure 9:
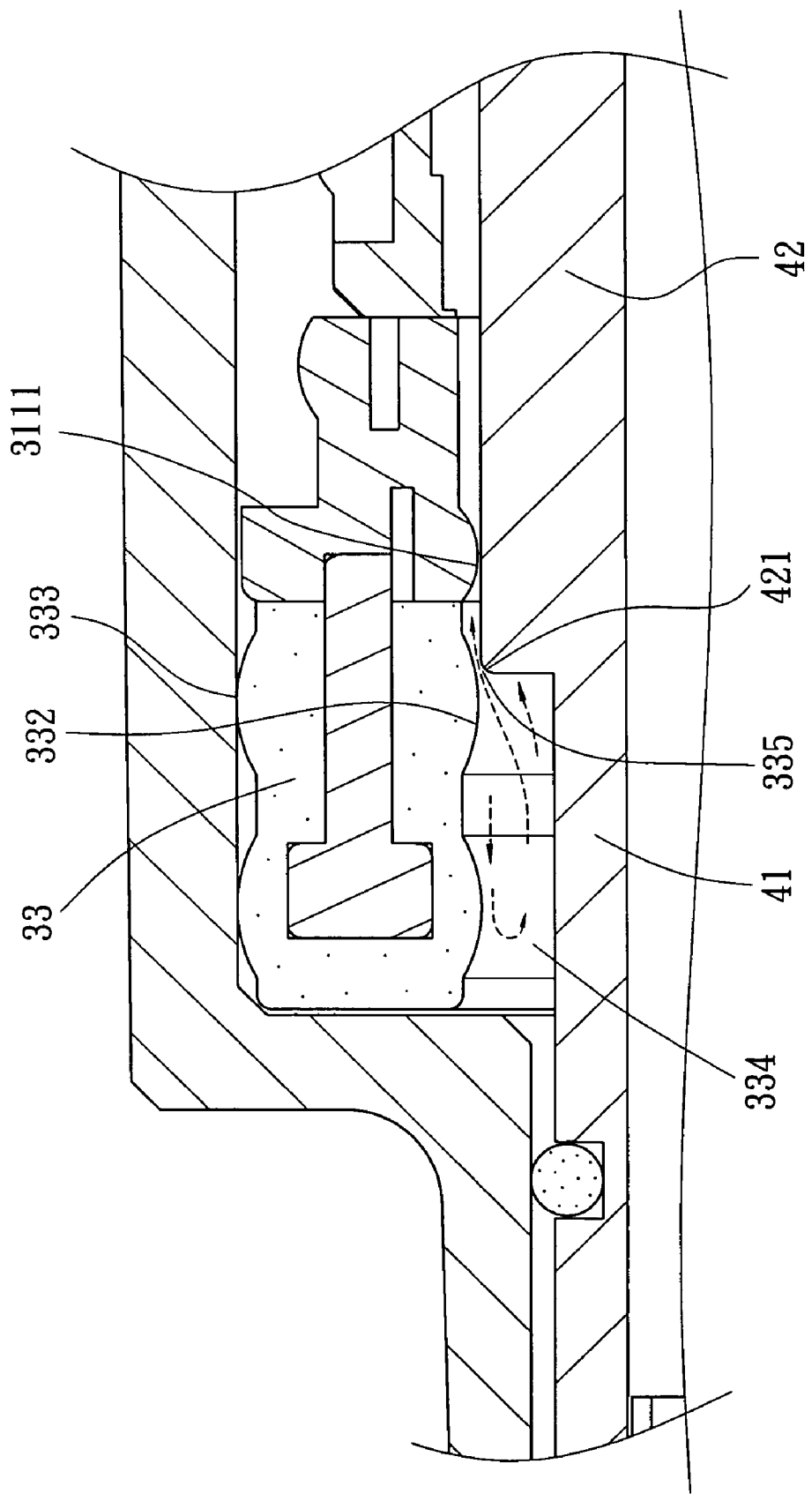
FIG. 9 is a schematic view of the invention with the air pressure in an instant releasing condition.
Figure 10:
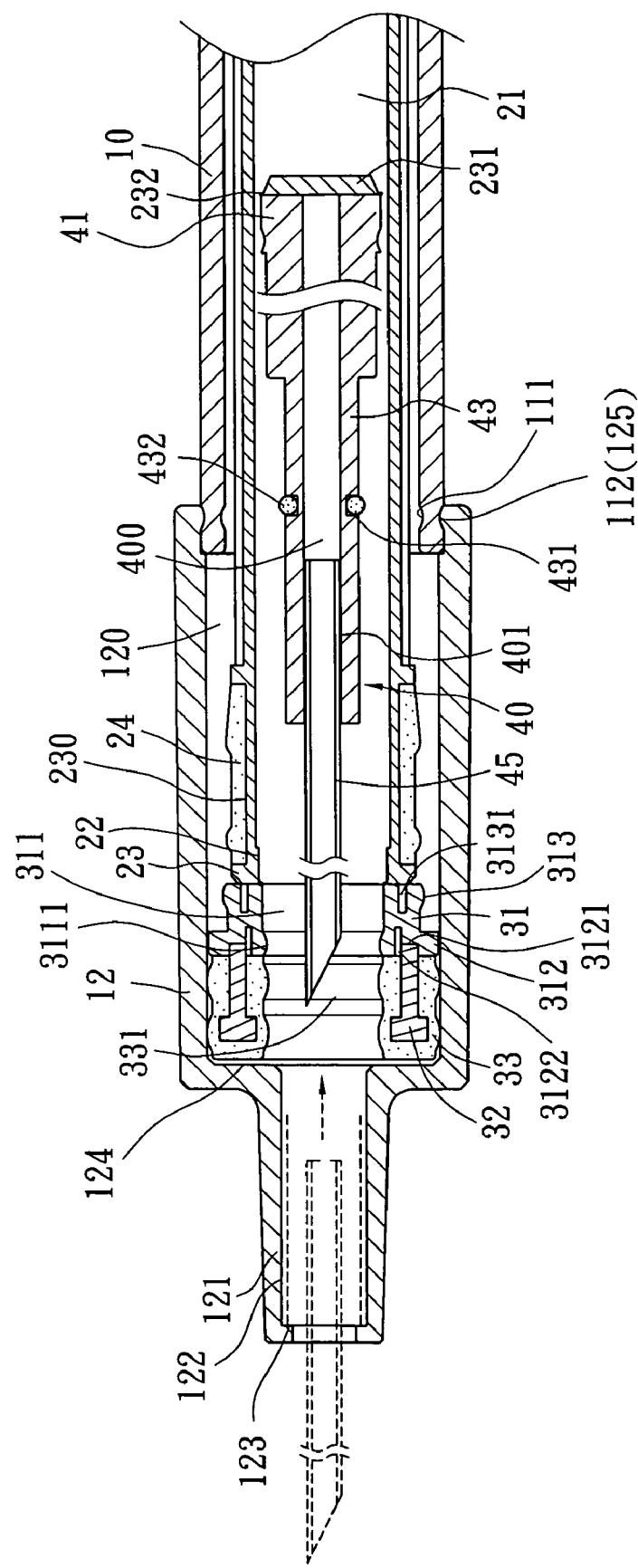
FIG. 10 is a schematic view of the invention with the needle mount held inside.

Refer to FIGS. 7, 8 and 9, when the safety syringe of the invention is in use, the push rod 20 is pushed forwards; the distal end 23 is moved from one end of the hollow passage 11 to another end. When the distal end 23 is pushed in contact with the first stem 41 of the needle mount 40, it presses one end of the first stem 41 until the cut surface 231 is ruptured. Due to the indented rim 232 the thickness of the cut surface 231 is thinner, hence after receiving a pressing force the breaking surface 231 is broken and separated from the distal end 23. With the distal end 23 moved forwards continuously, the inner detent member 31 and piston rubber ring 33 of the driving module 30 compress air to generate air pressure. When the piston rubber ring 33 and the needle mount 40 are separated abruptly and moved to the top portion of the housing chamber 120 of the barrel cover 12, the jutting ring 332 and the third stem 43 form a space 334 between them, and a gap 335 is formed between the jutting ring 332 and one end 421 of the second stem 42 so that air pressure (referring to the arrow in FIG. 9) is released instantly from the space 334 through the gap 335. Meanwhile, the second stem 42 held in the housing chamber 120 is retracted into the holding chamber 21 of the push rod 20 as shown in FIG. 10. Thus the needle 45 is held safely after injection.

Figure 11:
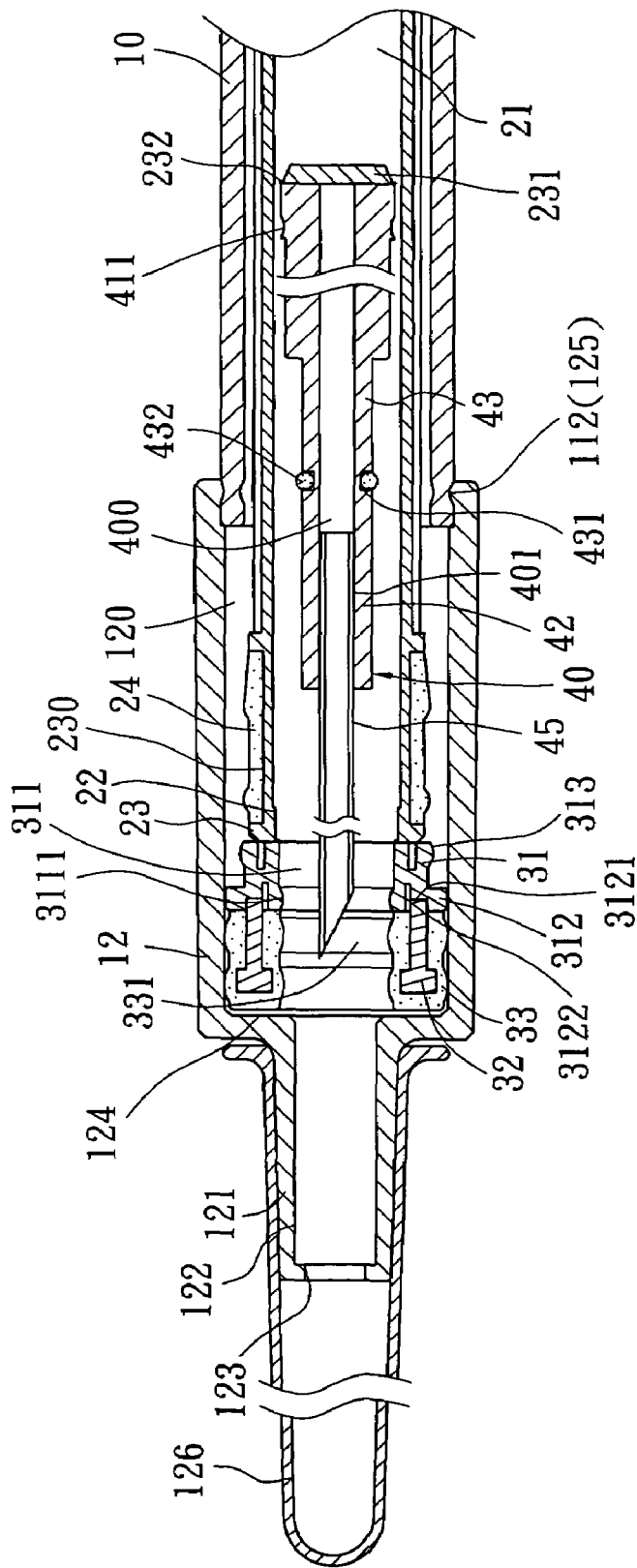
FIG. 11 is a schematic view of the invention with the barrel cover covered by an upper cap.

The protruding end 121 of the barrel cover 12 may also be protected from hurting people after the needle 45 is held in the holding chamber 21. Referring to an embodiment shown in FIG. 11. An upper cap 126 is provided to encase the protruding end 121 to cover the through hole 122 so that the needle 45 can be prevented from slipping out of the protruding end 121 again after retracted and stored. Such a design can enhance safety without hurting people during recycling and transportation.

By means of the construction set forth above, after the safety syringe is used the needle 45 can be stored safely without hurting people. By pushing the push rod 20 the distal end 23 presses the inner detent member 31 and piston rubber ring 33 forwards so that the cut surface 231 of the distal end 23 is thrust by one end of the first stem 41. Due to the thinner thickness formed by the indent rim 232 on the cut surface 231, the distal end 23 can be ruptured and separated; and the continuous moving forward of the push rod 20 can instantly release the air pressure to retract the second stem 42 and hold the needle mount 40 in the holding chamber 21 of the push rod 20. As a result, the needle 45 can be safely stored to enhance safety.

What is claimed is:

1. A safety syringe, comprising:
    a barrel which has a hollow passage inside and one end formed with annular grooves on an inner wall and an outer wall thereof opposing each other and coupled with a barrel cover which has a protruding end with a housing chamber formed therein;
    a push rod which is held in the hollow passage in a close contact and slidable manner and has a holding chamber with a bucking surface formed thereon and a distal end with an annular trough formed on the periphery and an indented rim and a cut surface formed at two end surfaces thereof;
    a driving module which is held in the barrel cover and includes an inner detent member, a piston seat and a piston rubber ring, the inner detent member having an aperture, an annular bulged element and an annular ring at one end, the piston seat being protrusive and having one end wedged in one end of the inner detent member, the piston rubber ring being adjacent to the inner detent member; and
    a needle mount which is coupled with the inner detent member and held in the piston rubber ring and has a first stem, a second stem and a third stem of different diameters at one end, the first stem being coupled with the annular bulged element of the inner detent member, the second stem having one end inserted in the piston rubber ring, the third stem being coupled with the protruding end of the barrel cover, whereby the push rod is movable forwards to push the inner detent member and the piston rubber ring of the driving module forwards to make a cut surface at one end of the push rod to hit one end of a first stem of the needle mount to be broken and separated so that continuous moving forward of the push rod causes instant release of air pressure inside to retract the needle mount in a holding chamber of the push rod to safely hold a needle after injection.

2. The safety syringe of claim 1, wherein the protruding end of the barrel cover has a through hole inside, the through hole having a first pressing surface and a second pressing surface.

3. The safety syringe of claim 2, wherein the second pressing surface is formed at a diameter greater than that of the first pressing surface.

4. The safety syringe of claim 1, wherein the inner detent member has a wedge groove and an extensible first groove at one end close to the annular ring, and a flange at another end wedged in the annular groove of the barrel and an second extensible groove formed on the surface of the another end.

5. The safety syringe of claim 1, wherein the piston rubber ring is coupled with a piston seat without deforming.

6. The safety syringe of claim 1, wherein the piston rubber ring has a through hole formed therein and the periphery coupled with at least one jutting rings.

7. The safety syringe of claim 1, wherein the first stem, the second stem and the third stem have a through hole formed inside and a holding port at one end of the through hole to hold a needle.

8. The safety syringe of claim 1, wherein the third stem has an annular groove on the periphery to hold an O-ring.

* * * * *